United States Patent [19]

Krüger et al.

[11] 4,421,694
[45] Dec. 20, 1983

[54] PROCESS FOR THE PREPARATION OF NITROANILINES

[75] Inventors: Bruno Krüger, Cologne; Adolf Winkler, Leverkusen; Günter Hentze, Odenthal, all of Fed. Rep. of Germany

[73] Assignee: Bayer Aktiengesellschaft, Leverkusen, Fed. Rep. of Germany

[21] Appl. No.: 340,901

[22] Filed: Jan. 20, 1982

[30] Foreign Application Priority Data

Feb. 7, 1981 [DE] Fed. Rep. of Germany ....... 3104310

[51] Int. Cl.³ .................... C07C 85/04; C07C 120/00
[52] U.S. Cl. ............................... 260/465 E; 564/406; 560/129; 562/433; 562/437
[58] Field of Search ................. 564/406; 260/465 E; 560/129; 562/433, 437

[56] References Cited

U.S. PATENT DOCUMENTS

| | | | |
|---|---|---|---|
| 3,959,377 | 5/1976 | Bil | 564/406 |
| 3,966,816 | 6/1976 | Woods et al. | 564/406 X |
| 4,328,369 | 5/1982 | Baldi et al. | 564/406 |

*Primary Examiner*—Paul F. Shaver
*Attorney, Agent, or Firm*—Sprung, Horn, Kramer & Woods

[57] ABSTRACT

The invention relates to a process for the preparation of nitroanilines by the reaction of chloronitrobenzenes with ammonia at elevated temperature and under elevated pressure, and in the presence of chlorinated aromatic hydrocarbons.

Nitroanilines are important precursors and intermediate products for the preparation of dyestuffs, pharmaceuticals and plant protection agents.

13 Claims, No Drawings

PROCESS FOR THE PREPARATION OF NITROANILINES

The present invention relates to a process for the preparation of nitroanilines by the reaction of chloronitrobenzenes with ammonia at elevated temperature and under elevated pressure.

The preparation of 5-chloro-2-nitroaniline by the reaction of 2,4-dichloronitrobenzene with alcoholic ammonia solution is known from Gazz.Chim.Ital. 4, 376 (1874). However, this procedure is associated with considerable deficiencies because the reaction component employed in excess, namely ammonia, and the solvent, namely the alcohol, are miscible with one another and can thus only be separated from each other and from the reaction product with considerable effort. The high volatility of the alcohol and its miscibility with water require, in addition, a great technical effort in order to maintain the purity of the air and of the water, adversely affecting the cost efficiency of this process.

Furthermore, the preparation of 5-chloro-2-nitroaniline by the reaction of 2,4-dichloronitrobenzene with aqueous ammonia is known from Recueil 72, 44 (1953). However, in this process, in addition to the desired 5-chloro-2-nitroaniline, considerable quantities of 2,4-diaminonitrobenzene are also formed, which is technically troublesome to separate off and which can only be separated off with an adverse effect on the yield of 5-chloro-2-nitroaniline. As experiments showed in addition, such reaction mixtures have only a limited thermal stability, so that carrying out this process on an industrial scale raises safety problems.

A process for the preparation of nitroanilines of the formula (I)

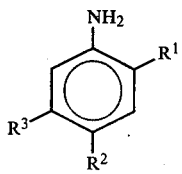

(I)

wherein
$R^1$ represents halogen, a cyano group, a nitro group, a carboxyl group, an acyl group or a sulpho group,
$R^2$ represents hydrogen, a nitro group or a carboxyl group and
$R^3$ denotes hydrogen or halogen,
and wherein
at least one of the radicals $R^1$ or $R^2$ represents a nitro group,
by the reaction of chloronitrobenzenes of the formula (II)

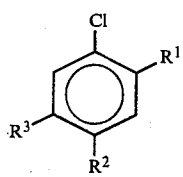

(II)

wherein $R^1$, $R^2$ and $R^3$ have the meaning given above, with ammonia, at elevated temperature and under elevated pressure, has now been found, which is characterized in that the reaction is carried out in the presence of a chlorinated aromatic hydrocarbon.

The following may be mentioned as halogens of the formula (I): fluorine, chlorine and bromine, preferably chlorine; those acyl radicals having 1 to 6 carbon atoms, such as the acetyl radical, the propionyl radical and the benzoyl radical, preferably the acetyl radical and the benzoyl radical may be mentioned as the acyl radicals.

Those chloronitrobenzenes of the formula (III)

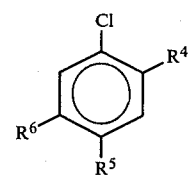

(III)

wherein
$R^4$ represents chlorine, a nitro group or a cyano group,
$R^5$ represents hydrogen, a nitro group or a carboxyl group and
$R^6$ denotes hydrogen or chlorine,
and wherein
at least one of the radicals $R^4$ or $R^5$ represents a nitro group,
are preferably reacted according to the process according to the invention.

2,4-Dichloronitrobenzene is particularly preferably employed in the process according to the invention.

Those hydrocarbons of the formula (IV)

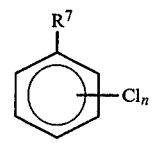

(IV)

wherein
$R^7$ denotes a lower alkyl radical or hydrogen and
n represents the number 1, 2 or 3,
can be employed in the process according to the invention as the chlorinated aromatic hydrocarbons.

Those alkyl radicals having 1 to 4, preferably 1 to 3, carbon atoms, such as the methyl, the ethyl, the n-propyl, the iso-propyl, the n-butyl, the iso-butyl and the tert.-butyl radical, preferably the methyl and the ethyl radical, may be mentioned as the lower alkyl radicals.

The following chlorinated aromatic hydrocarbons, which can also be used in a mixture with one another, are examples of suitable hydrocarbons: chlorobenzene, o-dichlorobenzene, m-dichlorobenzene, p-dichlorobenzene, o-, m-, p-chlorotoluene, 1,2,3-trichlorobenzene and 1,2,4-trichlorobenzene, preferably chlorobenzene and o-dichlorobenzene, particularly preferably chlorobenzene.

The quantity of chlorinated aromatic hydrocarbons can be varied within wide ranges. In general, the quantity of chlorinated aromatic hydrocarbons in proportioned such that an easily stirrable suspension is still obtained with the reaction product. The ratio by weight of chlorinated aromatic hydrocarbons to chloronitrobenzene is customarily about 1:4 to 4:1, preferably 1:2 to 2:1, and particularly preferably 1:1.

It is sufficient, for the reaction according to the invention, to employ 2 mols of ammonia per mol of starting material. However, it is advantageous to add a quantity of ammonia greater than the stoichiometric quantity in order to maintain a reaction pressure necessary for the reaction to proceed to completion. The molar ratio of starting material to ammonia can be about 1:3 to 1:10 in this reaction. The molar ratio of starting material to ammonia is preferably 1:4 to 1:8.

The process according to the invention is carried out, in general, at temperatures of from approximately 100° to 200° C., preferably at from 120° to 160° C. The process is carried out under an elevated pressure of from 10 to 100 bars, preferably from 20 to 40 bars.

The reaction time of the reaction according to the invention is dependent, inter alia, on the quantity of chlorinated aromatic hydrocarbons added, on the excess of ammonia, on the temperature and on the pressure, and is approximately 10 to 25 hours for a virtually complete conversion when the preferred values of the reaction parameters are observed.

The process according to the invention can be carried out in such a manner that the starting material is mixed with the chlorinated aromatic hydrocarbon, and, at room temperature or at the reaction temperature, the total quantity of ammonia provided for the reaction is added directly or only in portions. In a preferred embodiment, only a part of the ammonia is added at the reaction temperature until a pre-selected reaction pressure is reached, and the remainder of the ammonia is metered into the mixture at a rate corresponding to the rate at which it reacts.

The working-up of the reaction mixture and the isolation of the reaction product can be carried out according to customary processes. When the pressure in the reaction vessel is released, the ammonia employed in excess can be recovered, in an absorption apparatus, as aqueous ammonia, or can be obtained, in a pressure distillation, as anhydrous ammonia, and can again be employed in the process according to the invention.

The reaction product and the chlorinated aromatic hydrocarbons can be separated from one another by filtration or distillation of the remaining product suspension. A particularly advantageous working-up of the product mixture can be effected by means of a steam distillation. In this process, small quantities of unreacted starting material pass over with the chlorinated aromatic hydrocarbon employed. The chlorinated aromatic hydrocarbon containing a small quantity of starting material can be directly used again for subsequent mixtures. The product can be isolated by filtration from the aqueous product suspension obtained.

The advantage of the process according to the invention is to be seen, in particular, in the high selectivity with which the reaction proceeds, with virtually complete conversion. In the case of the amination of dihalogenonitrobenzenes, a diamination occurs only to a very minor extent, in contrast to the state of the art. Even in the case of relatively long reaction times and high excesses of ammonia, the formation of diaminonitrobenzenes remains negligibly small. Accordingly, the reaction mixtures obtained are thermally stable and show no tendency to undergo uncontrolled decomposition. The reaction product is produced in high purity and can be directly further processed as such. Separating off the chlorinated aromatic hydrocarbons from the ammonia and from the reaction product involves no technical difficulties and can be carried out in a simple manner.

Nitroanilines, particularly 5-chloro-nitroaniline, are important precursors and intermediate products for the preparation of dyestuffs, pharmaceuticals and plant protection agents (see, for example German Offenlegungsschrift No. 2,438,120, German Offenlegungsschrift No. 2,549,417, German Offenlegungsschrift Nos. 2,363,351 and German Offenlegungsschrift No. 2,332,343 and U.S. Pat. Nos. 3,929,821, 3,929,822, 3,929,824, 3,993,769, 3,993,768, 4,002,640, 4,031,234, 4,080,461 and 4,034,107).

The examples which follow are intended to illustrate the process according to the invention.

EXAMPLE 1

200 ml (8 mols) of anhydrous ammonia are added to 192 g (1 mol) of 2,4-dichloronitrobenzene in 400 ml of chlorobenzene at room temperature in an autoclave of high quality steel. The mixture is heated to 130° C., whilst stirring, and is kept at this temperature for 20 hours. The pressure decreases from its maximum value of 53.5 bars to 36.5 bars during the course of the reaction. After the mixture has been cooled and the pressure in the autoclave released, chlorobenzene is expelled with steam. The aqueous product suspension is filtered under suction at room temperature and the yellow crystalline product is washed with water until it is free of chloride. 162 g of product, with a content of 95.1%, are obtained after the drying process; this corresponds to a yield of 89.3%.

If ammonia is pumped into the autoclave in 2 portions of 100 ml each, and the mixture is allowed to react for 2 periods of 10 hours each at 130° C. and under pressures of from 34 to 25 bars and of from 42 to 37 bars, 172 g of a 93.4% strength product, corresponding to a yield of 93.1%, are obtained.

EXAMPLE 2

192 g (1 mol) of 2,4-dichloronitrobenzene are warmed with 200 ml of chlorobenzene to 140° C. in an autoclave of high quality steel. 150 ml (6 mols) of anhydrous ammonia are pumped into the autoclave, whilst stirring and maintaining the temperature at 140° C., at such a rate that a pressure of 35 bars is not exceeded. A total pumping time of 16 hours is required. The mixture is allowed to react further for another 5 hours at 140° C. The mixture is then cooled, the pressure in the autoclave is released and the content of the autoclave is rinsed into a distillation apparatus, using a total of 1 l of water. Chlorobenzene is now distilled off in this apparatus as an azeotropic mixture with water, and, after phase separation, is used again in the subsequent mixture. The aqueous product suspension is filtered under suction and the yellow crystalline product is dried in vacuo at 60° C.

From 6 identical mixtures, in which, however, the recovered chlorobenzene from the preceding mixture is always used as the diluent, a total of 1,025 g of 96% strength product are obtained, corresponding to a yield of 95.1%. By-products: 0.9% of 2,4-dichloronitrobenzene, 1.9% of 3-chloro-4-nitroaniline and 1.0% of 2,4-diaminonitrobenzene. Melting point 120° to 124° C.

EXAMPLE 3

307 g (1.6 mols) of 2,4-dichloronitrobenzene are heated with 320 ml of o-dichlorobenzene to 130° C. in an autoclave of high quality steel. 240 ml (9.6 mols) of ammonia are pumped into the autoclave at this temperature, during the course of 14 hours, at such a rate that a pressure of 35 bars is not exceeded. The mixture is further stirred for 5 hours at 130° C., and after it has been cooled and the pressure released from the autoclave, the total mixture is subjected to a steam distillation. After all the o-dichlorobenzene has been expelled, the product is isolated by filtration. 246 g of brownyellow product of melting point 121° to 123° C. with a purity of 95.7%, corresponding to a yield of 85.3%, are obtained.

EXAMPLE 4

302 g (1.5 mols) of 4-chloro-3-nitro-benzoic acid are suspended in 300 ml of chlorobenzene in an autoclave. 225 ml (9 mols) of ammonia are pumped into the autoclave at 120° C. at such a rate that a pressure of 20 bars is not exceeded. The mixture is further stirred for 10 hours at 120° C. The working-up process is carried out by releasing the pressure in the autoclave and subsequently subjecting the mixture to a steam distillation. 276.5 g of 93% strength product are obtained. This corresponds to a yield of 94%. Melting point 250°–252° C.

EXAMPLE 5

150 ml (6 mols) of ammonia are pumped, during the course of 40 minutes at 130° C., into a mixture of 182.5 g (1 mol) of 2-cyano-4-nitrochlorobenzene and 400 ml of chlorobenzene, the mixture being stirred in an autoclave. The maximum pressure is 25 bars. The mixture is further stirred for 4 hours at 130° C. and is then worked up in a customary manner. 162 g of a 98% strength product, corresponding to a yield of 97%, are obtained. The solidification point is 207.5° C.

EXAMPLE 6

288 g (1.5 mols) of 3,4-dichloronitrobenzene in 300 ml of chlorobenzene are reacted with 225 ml (9 mols) of ammonia at 160° C. in an autoclave. The pumping time was 9 hours, and the mixture was further stirred for 15 hours. During this time the pressure decreased from 57 to 43 bars.

Yield: 243 g of crude product of melting point 101°–103° C.; gas chromatographic analysis: 93.4% strength=87.7% of theory.

EXAMPLE 7

A mixture of 315 g (2 mols) of 2-nitrochlorobenzene and 300 ml of chlorobenzene is heated to 160° C. in a 1.3 l autoclave of high quality steel. 300 ml (12 mols) of anhydrous ammonia are pumped into the autoclave at this temperature, the pressure increasing to 70 bars. The pressure decreases to 48 bars during the course of 20 hours at 160° C. After the pressure has been released in the autoclave and 1,000 ml of water have been added to the mixture, chlorobenzene is distilled off together with water. An oil remains, which solidifies, on cooling, to give dark yellow crystals. The product is filtered off under suction from the aqueous phase at room temperature and is dried in the air. 270 g of crude product of melting point 66°–68° C. are obtained. According to gas chromatographic analysis, the product is 93.5% strength, corresponding to a yield of 91.5%.

EXAMPLE 8

202.5 g (1 mol) of 2,4-dinitrochlorobenzene in 400 ml of chlorobenzene are initially introduced into an autoclave. 110 ml (4.4 mols) of ammonia are pumped into the autoclave at 100° C. during the course of 4 hours. The mixture is further stirred for another hour at 100° C., and is then worked up by releasing the pressure in the autoclave and subjecting the mixture to a steam distillation. 181 g of 98% strength product of melting point 177°–179° C., corresponding to a yield of 97%, are obtained.

What is claimed is:

1. A process for the preparation of a nitroaniline of the formula

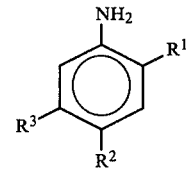

wherein
$R^1$ represents halogen, a cyano group, a nitro group, a carboxyl group, an acyl group or a sulpho group,
$R^2$ represents hydrogen, a nitro group or a carboxyl group and
$R^3$ denotes hydrogen or halogen,
and wherein
at least one of the radicals $R^1$ or $R^2$ represents a nitro group,
which comprises contacting a chloronitrobenzene of the formula

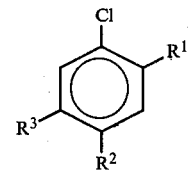

wherein $R^1$, $R^2$ and $R^3$ have the meaning given above, with ammonia, at elevated temperature and under elevated pressure in the presence of a chlorinated aromatic hydrocarbon.

2. A process according to claim 1, wherein said chlorinated hydrocarbon has the formula

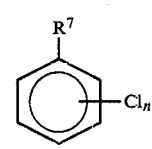

wherein
$R^7$ denotes a lower alkyl radical or hydrogen and
n represents 1, 2 or 3.

3. A process according to claim 1, wherein said chlorinated aromatic hydrocarbon is o-dichlorobenzene, m-dichlorobenzene, p-dichlorobenzene, chlorobenzene, o-, m-, p-chlorotoluene, 1,2,3-trichlorobenzene and/or 1,2,4-trichlorobenzene.

4. A process according to claim 1, wherein said chlorinated aromatic hydrocarbon is chlorobenzene or o-dichlorobenzene.

5. A process according to claim 1, wherein said chlorinated aromatic hydrocarbon is employed in a weight ratio of 1:4 to 4:1 to the chloronitrobenzene.

6. A process according to claim 1, wherein the chlorinated aromatic hydrocarbon is present in a weight ratio to 1:2 to 2:1 to the chloronitrobenzene.

7. A process according to claim 1, wherein the chlorinated aromatic hydrocarbon is present in a weight ratio of 1:1 to the chloronitrobenzene.

8. A process according to claim 1, wherein said chloronitrobenzene is 2,4-dichloronitrobenzene.

9. A process according to claim 1, wherein said chloronitrobenzene is 4-chloro-3-nitro-benzoic acid.

10. A process according to claim 1, wherein said chloronitrobenzene is 2-cyano-4-nitrochlorobenzene.

11. A process according to claim 1, wherein said chloronitrobenzene is 3,4-dichloronitrobenzene.

12. A process according to claim 1, wherein said chloronitrobenzene is 2-nitrochlorobenzene.

13. A process according to claim 1, wherein said chloronitrobenzene is 2,4-dinitrochlorobenzene.

* * * * *